United States Patent
Lee et al.

(10) Patent No.: US 10,092,261 B2
(45) Date of Patent: Oct. 9, 2018

(54) X-RAY IMAGING APPARATUS AND CONTROL METHOD FOR THE SAME

(71) Applicant: SAMSUNG ELECTRONICS CO., LTD., Suwon-si (KR)

(72) Inventors: Jong Ha Lee, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1175 days.

(21) Appl. No.: 14/286,260

(22) Filed: May 23, 2014

(65) Prior Publication Data

US 2014/0348291 A1   Nov. 27, 2014

(30) Foreign Application Priority Data

May 23, 2013   (KR) .................. 10-2013-0058351

(51) Int. Cl.
*A61B 6/00* (2006.01)
*A61B 6/04* (2006.01)

(52) U.S. Cl.
CPC ............ *A61B 6/502* (2013.01); *A61B 6/0414* (2013.01)

(58) Field of Classification Search
CPC ............................. A61B 6/0414; A61B 6/502
See application file for complete search history.

(56) References Cited

U.S. PATENT DOCUMENTS

| 5,590,166 A | 12/1996 | Suni et al. |
| 2005/0008117 A1 | 1/2005 | Livingston |
| 2006/0165215 A1 | 7/2006 | Galkin |
| 2008/0043904 A1 * | 2/2008 | Hoernig .............. A61B 6/0414 378/37 |
| 2009/0190715 A1 | 7/2009 | Meer et al. |
| 2014/0135623 A1 * | 5/2014 | Manak ................. A61B 8/4416 600/427 |
| 2014/0328458 A1 * | 11/2014 | Erhard ................. A61B 6/0414 378/37 |

FOREIGN PATENT DOCUMENTS

| KR | 10-1168308 B1 | 7/2012 |
| KR | 10-1342812 B1 | 12/2013 |

* cited by examiner

*Primary Examiner* — Dani Fox
(74) *Attorney, Agent, or Firm* — Sughrue Mion, PLLC

(57) ABSTRACT

Provided is an X-ray imaging apparatus including an X-ray source to emit an X-ray onto a breast, a detector assembly configured to detect the X-ray transmitted through the breast, a compression paddle configured to compress the breast positioned on the detector assembly, a paddle manipulator configured to control the compression paddle according to a command, a degree-of-compression sensor configured to measure a degree of compression to which the breast is compressed by the compression paddle, and a pressure controller configured to supply a pressure corresponding to the measured degree of compression of the breast to the paddle manipulator.

20 Claims, 17 Drawing Sheets

OFF STATE

ON STATE

OFF STATE

ON STATE

OFF STATE

ON STATE

X-RAY IMAGING APPARATUS AND CONTROL METHOD FOR THE SAME

CROSS-REFERENCE TO RELATED APPLICATION(S)

This application claims priority from Korean Patent Application No. 10-2013-0058351, filed on May 23, 2013, in the Korean Intellectual Property Office, the disclosure of which is incorporated herein by reference in its entirety.

BACKGROUND

1. Field

Apparatuses and methods consistent with exemplary embodiments relate to an X-ray imaging apparatus which produces an X-ray image by transmitting X-rays through an object and a control method for the same.

2. Description of the Related Art

An X-ray imaging apparatus is designed to emit X-rays onto an object and acquire an image of an internal structure of the object using X-rays transmitted through the object. Since transmittance of X-rays depends on properties of materials which constitute the object, an image of the inner structure of the object may be obtained by detecting an intensity or strength of the X-rays transmitted through the object.

An X-ray imaging apparatus for breast imaging is structurally different from X-ray imaging apparatuses for imaging other tissues. Since a breast includes a larger amount of glandular tissue and fatty tissue, X-ray imaging needs to be performed while the breast is positioned between an X-ray source and an X-ray detector and compressed by a compression paddle, to obtain a sharp X-ray image showing the internal structure of the breast. To this end, the breast is positioned on an upper portion of a Bucky and compressed with the compression paddle.

A degree of compression of the breast may be displayed as numerical information. A radiologic technologist who manipulate the compression paddle may determine a current degree of compression of the breast based on the numerical information and adjust the degree of compression. However, in a case where the degree of compression of the breast is provided only in a form of numerical information, the radiologic technologist may not accurately comprehend the degree of compression felt by a patient. In addition, in a case where the radiologic technologist fails to view a screen which displays the degree of compression while performing other operations such as adjusting a position of the breast, compression may not be smoothly performed.

SUMMARY

One or more exemplary embodiments provide an X-ray imaging apparatus and a control method for the same, in which a user may feel a degree of compression of a breast which a patient may feel by transferring pressure corresponding to the degree of compression of the breast to the user, thereby providing more accurate compression considering a condition of the patient.

In accordance with an aspect of an exemplary embodiment, an X-ray imaging apparatus to capture an X-ray image of an object includes an X-ray source configured to emit an X-ray onto the object, a detector assembly configured to detect the X-ray transmitted through the object, a compression paddle configured to compress the object positioned on the detector assembly, a paddle manipulator configured to control the compression paddle according to a command, a degree-of-compression sensor configured to measure a degree of compression to which the object is compressed by the compression paddle, and a pressure controller configured to supply a pressure corresponding to the measured degree of compression of the object to the paddle manipulator.

The paddle manipulator may include a fluid accommodation portion configured to accommodate a fluid therein, wherein the pressure controller may control an amount of the fluid accommodated in the fluid accommodation portion according to the degree of compression of the object.

The fluid accommodation portion may include at least one from among a hydraulic cylinder and a gas spring.

The paddle manipulator may further include an upper plate to which external force is applied and the fluid accommodation portion may be positioned on a surface of the upper plate.

The paddle manipulator may include a foot pedal.

The pressure controller may supply a pressure substantially linearly proportional to the degree of compression of the object to the paddle manipulator.

A proportionality constant between the degree of compression of the object and the pressure supplied to the paddle manipulator may be greater than 0 and equal to or less than 1.

The pressure controller may supply the pressure corresponding to the degree of compression of the object to the paddle manipulator such that a rate of increase of the pressure supplied to the paddle manipulator decreases in response to an increase in the degree of compression of the object.

The pressure controller may supply the pressure corresponding to the degree of compression of the object to the paddle manipulator such that a rate of increase of the pressure supplied to the paddle manipulator increases in response to an increase in the degree of compression of the object.

The degree-of-compression sensor may include at least one from among a force sensor and a pressure sensor.

The degree-of-compression sensor may be mounted on the compression paddle.

The degree-of-compression sensor may measure the degree of compression of the object in real time or at a certain time interval.

The X-ray imaging apparatus may further include a display configured to numerically display the measured degree of compression of the object.

In accordance with an aspect of another exemplary embodiment, provided is a control method of an X-ray imaging apparatus including a compression paddle configured to compress an object, and a paddle manipulator configured to control the compression paddle according to a command. The control method includes moving, by the paddle manipulator, the compression paddle according to the command to compress the object, measuring a degree of compression of the object, and supplying a pressure corresponding to the measured degree of compression of the object to the paddle manipulator.

The measuring may be performed in real time or at a certain time interval.

The supplying may include supplying a pressure substantially linearly proportional to the degree of compression of the object.

The supplying may include supplying a pressure to the paddle manipulator such that a rate of increase of the pressure supplied to the paddle manipulator increases or decreases in response to an increase of the degree of compression.

In accordance with an aspect of another exemplary embodiment, provided is an apparatus for controlling positioning a compression paddle to compress an object placed on a support base for use in an X-ray imaging apparatus. The apparatus includes a paddle manipulator configured to control positioning the compression paddle according to an input from a user; a sensor configured to sense a pressure applied to the object by the compression paddle; and a controller configured to output to the user a tactile feedback corresponding to the sensed pressure.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
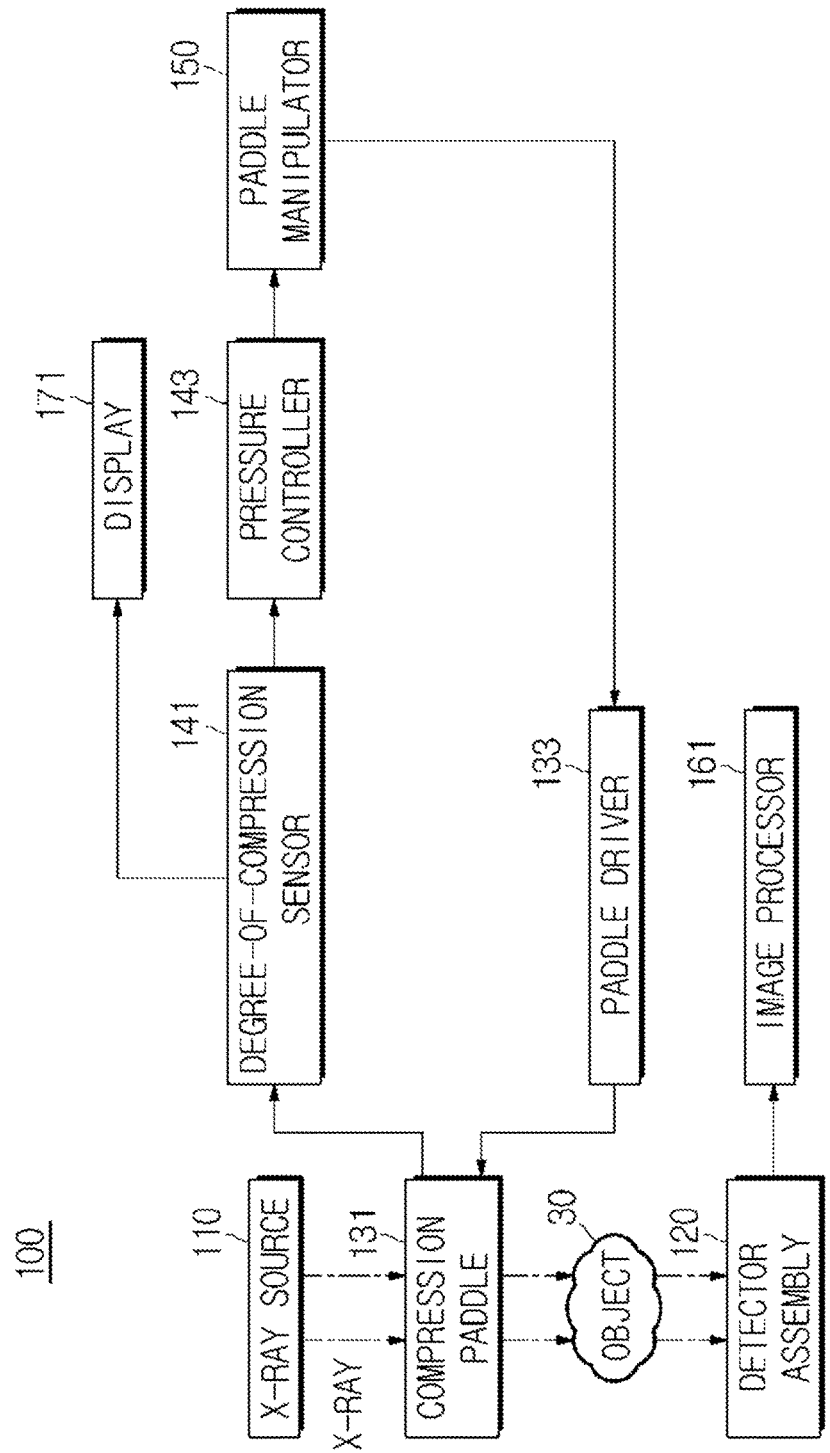
FIG. 1 is a control block diagram illustrating an X-ray imaging apparatus according to an exemplary embodiment.

Reference will now be made in detail to certain exemplary embodiments, which are illustrated in the accompanying drawings, wherein like reference numerals refer to like elements throughout.

FIG. 1 is a control block diagram illustrating an X-ray imaging apparatus according to an exemplary embodiment.

Referring to FIG. 1, an X-ray imaging apparatus 100 includes an X-ray source 110 to generate X-rays and emit the same onto an object 30, a detector assembly 120 to detect the X-rays transmitted through the object 30, a compression paddle 131 to compress the object 30, a paddle driver 133 to drive the compression paddle 131, a paddle manipulator 150 to control movement of the compression paddle 131 according to user manipulation, a degree-of-compression sensor 141 to measure a degree of compression of the object 30, and a pressure controller 143 to apply pressure corresponding to the measured degree of compression to the paddle manipulator 150.

Figure 2A:
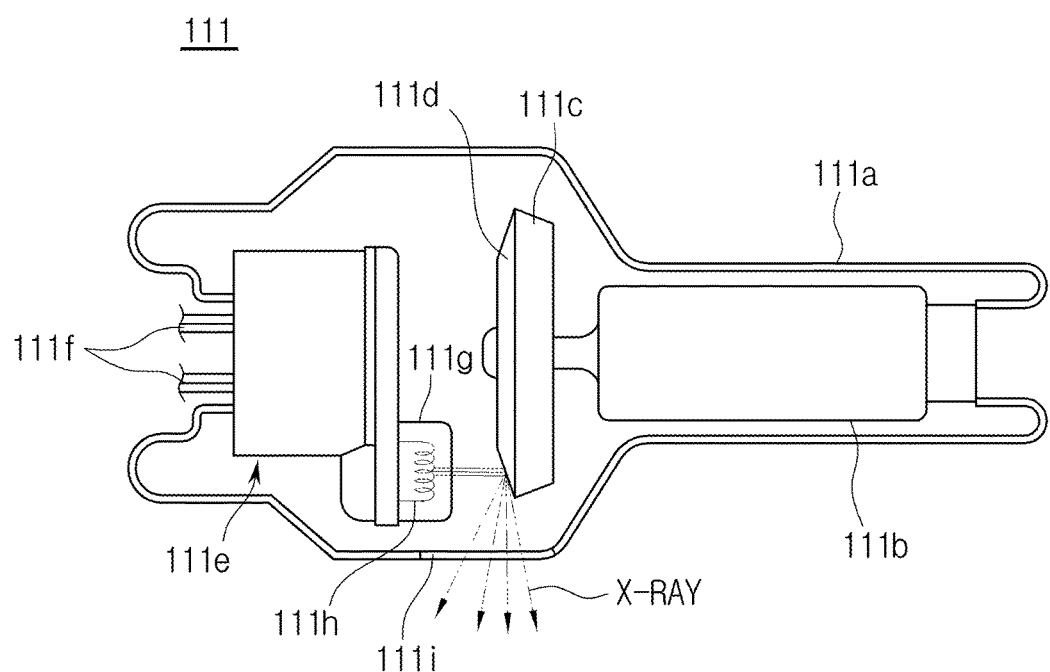
FIG. 2A is a schematic view illustrating a configuration of an X-ray tube according to an exemplary embodiment.
Figure 2B:
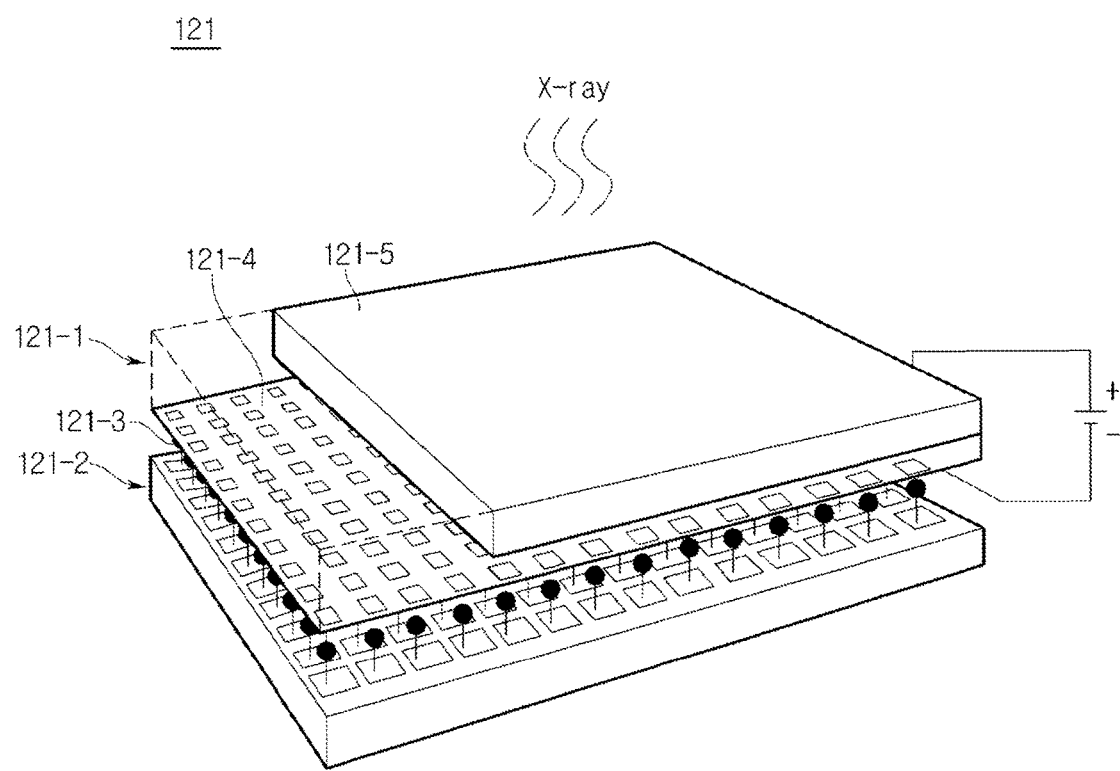
FIG. 2B is a schematic view illustrating a configuration of an X-ray detector according to an exemplary embodiment.

FIG. 2A is a schematic view illustrating a configuration of an X-ray tube according to an exemplary embodiment, FIG. 2B is a schematic view illustrating a configuration of an X-ray detector according to an exemplary embodiment.

The X-ray source 110 includes an X-ray tube 111 to generate an X-ray, which is also referred to as an X-ray tube head or an X-ray tube assembly. Referring to FIG. 2A, the X-ray tube 111 may be realized as a tube 111a containing two electrodes including an anode 111c and a cathode 111e. The X-ray tube 111 may be a glass tube comprising, for example, hard silica glass.

The cathode 111e includes a filament 111h and a focusing electrode 111g to focus electrons. The focusing electrode 111g is also referred to as a focusing cup. By creating a higher vacuum of pressure about 10 mmHg in the glass tube 111a and heating the filament 111h of the cathode 111e, thermal electrons are generated. A tungsten filament may be used as the filament 111h. The filament 111h may be heated by applying current to an electric wire 111f connected to the filament 111h.

The anode 111c may comprise copper. A target material 111d is applied to or disposed on a side of the anode 111c facing the cathode 111e. The target material may comprise a material having higher resistance such as, for example, chromium (Cr), iron (Fe), cobalt (Co), nickel (Ni), tungsten (W), and molybdenum (Mo). The higher the melting point of the target material is, the smaller the size of the focal spot may be.

When a higher voltage is applied between the cathode 111e and the anode 111c, thermal electrons are accelerated to collide with the target material 111d of the anode 111c to produce X-rays. The produced X-rays are emitted outside through a window 111i. The window 111i may comprise a thin film of beryllium (Be). Herein, a filter (not shown) may be positioned at a front or a rear surface of the window 111i to filter out X-rays in a specific energy band.

The target material 111d may be rotated by a rotor 111b. When the target material 111d is rotated, a heat storage capacity per unit area may be increased by more than about 10 times from the heat storage capacity per unit area obtained by fixing the target material 111d, and the size of the focal spot may be reduced.

The voltage applied between the cathode 111e and anode 111c of the X-ray tube 111 is referred to as tube voltage, and the magnitude thereof may be represented by a peak kilovoltage (kVp). Increase in the tube voltage may lead to increase in a speed of thermal electrons, thereby resulting in increase in energy of the X-rays (i.e., photon energy) produced when thermal electrons strike the target material. Electric current flowing through the X-ray tube 111 is referred to as tube current and may be represented by average current (mA). Increase in the tube current may lead to increase in a dose of X-rays (i.e., the number of X-ray photons).

The energy of the X-rays may be controlled with the tube voltage, and the intensity or dose of X-rays may be controlled with the tube current and X-ray exposure time. Therefore, the energy and dose of X-rays to be emitted may be controlled according to a type and properties of the object 30.

In a case where the emitted X-rays are in a certain energy band, the energy band may be defined by upper and lower limits. The upper limit of the energy band, i.e., a maximum energy of the emitted X-rays may be adjusted by adjusting the tube voltage, and the lower limit of the energy band, i.e., a minimum energy of the emitted X-rays may be adjusted by the filter. By filtering out X-rays in a low energy band by using the filter, the average energy of the emitted X-rays may be increased.

Additionally, although not shown in FIGS. 2A and 2B, the X-ray source 110 may further include a collimator disposed on a surface of the window 111i. The collimator may adjust an emission area over which the X-ray tube 111 emits X-rays, and may reduce scattering of X-rays.

When the X-rays are emitted from the X-ray source 110 to the object 30, the X-rays transmitted through the object 30 are detected by the detector assembly 120. The detector assembly 120 may include an X-ray detector 121 to detect X-rays.

Generally, the X-ray detector 121 may be classified according to a material thereof, a conversion technique used to convert the detected X-rays into an electrical signal, and a technique for acquiring an image signal.

For example, the X-ray detector 121 may be divided into a homogeneous type configured with homogeneous elements and a heterogeneous type configured with heterogeneous elements.

In a case where the X-ray detector 121 is configured with homogeneous elements, a portion of the X-ray detector 121 to detect X-rays to generate an electrical signal and a portion of the X-ray detector 121 to read and process the electrical signal may comprise a semiconductor of the same material, or manufactured in the same process. For example, the X-ray detector 121 may be configured with a light-receiving element such as, for example, a charge coupled device (CCD) or a complementary metal oxide semiconductor (CMOS).

In a case where the X-ray detector 121 is configured with heterogeneous elements, the portion of the X-ray detector 121 to detect X-rays to generate an electrical signal and the portion of the X-ray detector 121 to read and process the electrical signal may comprise different materials, or manufactured in different processes. In an example, a light-receiving element such as a photodiode or CdZnTe may be used to detect X-rays, while a CMOS readout integrated circuit (CMOS ROIC) is used to read and process an electrical signal. In another example, a strip detector may be used to detect X-rays, while the CMOS ROIC is used to read and process an electrical signal. In a further example, X-rays may be detected using an a-Si or a-Se flat panel system.

In addition, the X-ray detector 121 may be divided into a direct conversion type and an indirect conversion type depending on a technique for converting X-rays into an electrical signal.

In a direct conversion technique, when X-rays are emitted onto a light-receiving element, electron-hole pairs are temporarily generated in the light-receiving element. Holes move toward the cathode, and electrons move toward the anode, due to an electric field applied to the light-receiving element. The X-ray detector 121 may convert the movement of the electrons and the holes into an electrical signal. In the direct conversion technique, materials used for the light-receiving element may include, for example, a-Se, CdZnTe, $HgI_2$, and $PbI_2$.

In an indirect conversion technique, a scintillator is provided between the light-receiving element and the X-ray source. When photons with wavelengths in a range of visible light are produced through reaction between X-rays emitted from the X-ray source and the scintillator, the light-receiving element senses the photons and converts the same into an electrical signal. Materials used for the light-receiving element adopted in the indirect conversion technique may include, for example, a-Si. In addition, the scintillator may use a thin film-shaped gadolinium oxysulfide (Gadox) scintillator and a micro-column-shaped or needle-shaped CSI (T1).

In addition, depending on a technique for acquiring an image signal, the X-ray detector 121 may be divided according to a charge integration mode and a photon counting mode. In the charge integration mode, charges are stored for a certain period of time and a signal is acquired from the charges. In the photon counting mode, whenever a signal is produced by a single X-ray photon, photons having energy equal to or higher than a threshold energy are counted.

Any of the above techniques may be applicable to the X-ray imaging apparatus 100 of an exemplary embodiment to provide the X-ray detector 121. Moreover, exemplary embodiments are not limited to the above techniques. Other techniques in which X-rays are detected and converted into an electrical signal to acquire an image signal may be also applicable.

Hereinafter, a structure of the X-ray detector 121 which employs the direct conversion technique for directly acquiring an electrical signal from X-rays and a hybrid technique for combining a light-receiving element for detecting X-rays with a read circuit chip will be described in detail.

Referring to FIG. 2B, the X-ray detector 121 includes a light-receiving element 121-1 to detect X-rays and convert the same into an electrical signal, and a read circuit 121-2 to read an electrical signal. Here, the read circuit 121-2 may be configured in a form of a two-dimensional pixel array including a plurality of pixel areas. The light-receiving element 121-1 may comprise a single-crystal semiconductor material to secure higher resolution, fast response time and a higher dynamic range with lower energy and a low dose of radiation. The single-crystal semiconductor material may include, for example, germanium (Ge), cadmium telluride (CdTe), cadmium zinc telluride (CdZnTe), and gallium arsenide (GaAs).

The light-receiving element 121-1 may be provided as a PIN photodiode by coupling a p-type layer 121-4 configured as a two-dimensional array of p-type semiconductors to an n-type semiconductor substrate 121-5 having a higher resistance. The read circuit 121-2 which employs a CMOS process is connected to the light-receiving element 121-1 for each pixel, and the CMOS read circuit 121-2 and the light-receiving element 121-1 may be connected to each other through flip chip bonding. The CMOS read circuit 121-2 and the light-receiving element 121-1 may be connected to each other by forming a bump 121-3 comprising, for example, solder (PbSn) and indium (In) and reflow soldering of pressing the CMOS read circuit 121-2 and the light-receiving element 121-1 against each other with heat applied thereto. The structure described above is given only as an example of the X-ray detector 121, and exemplary embodiments are not limited thereto.

Although not shown in FIGS. 2A and 2B, an X-ray grid to prevent scattering of X-rays may be disposed at a surface of the X-ray detector 121.

When X-ray photons are incident on the light-receiving element 121-1, electrons in a valence band receive energy of the photons to be excited into a conduction band across a band gap. Thereby, electron-hole pairs are produced in a depletion region.

When metal electrodes are provided on the p-type layer 121-4 and n-type substrate 121-5 of the light-receiving element 121-1 and reverse bias is applied thereto, electrons of the produced electron-hole pairs in the depletion region are drawn to the n-type region, and the holes of the electron-hole pairs are drawn to the p-type region. The holes drawn to the p-type region are input to the read circuit 121-2 through the bump 121-3 such that the holes are read as an electrical signal produced by the photons. However, depending on the structure of the light-receiving element 121-1 and the applied voltage, electrons may be input to the read circuit 121-2 to produce an electrical signal.

The read circuit 121-2 may have a structure of a two-dimensional pixel array corresponding to the p-type semiconductor 121-4 of the light-receiving element 121-1, and each pixel reads an electrical signal. When charges are input from the light-receiving element 121 to the read circuit 121-2 through the bump 121-3, the read circuit 121-2 outputs an image signal represented by a voltage signal or the number of photons according to the configuration thereof.

The image signal output from the X-ray detector 121 is input to an image processor 161. The image signal is processed by the image processor 161 to produce an X-ray image of the object 30, e.g., a breast.

The image processor 161 may include one or more hardware and/or software components. For example, the image processor 161 may include one or more of an integrated circuitry, a dedicated circuit, firmware, and/or a processor such as a central processing unit (CPU) which executes software programs stored in a storage, e.g., a memory.

Figure 3:
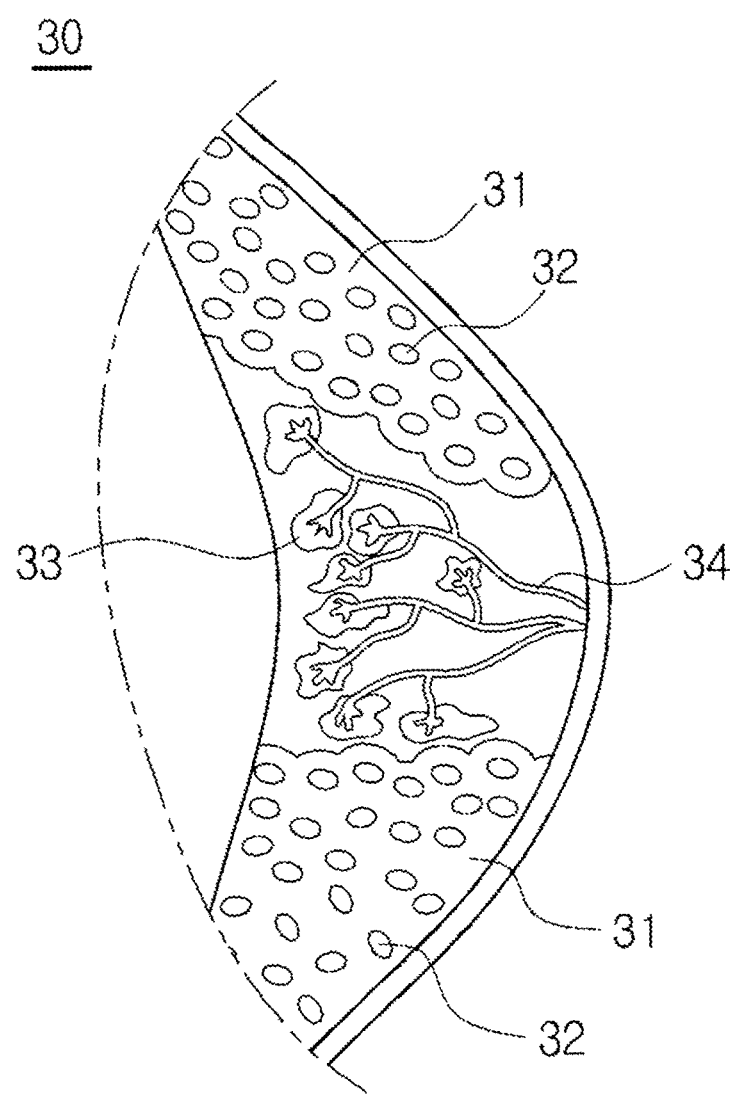
FIG. 3 is a schematic view illustrating an internal structure of a breast.
Figure 4:
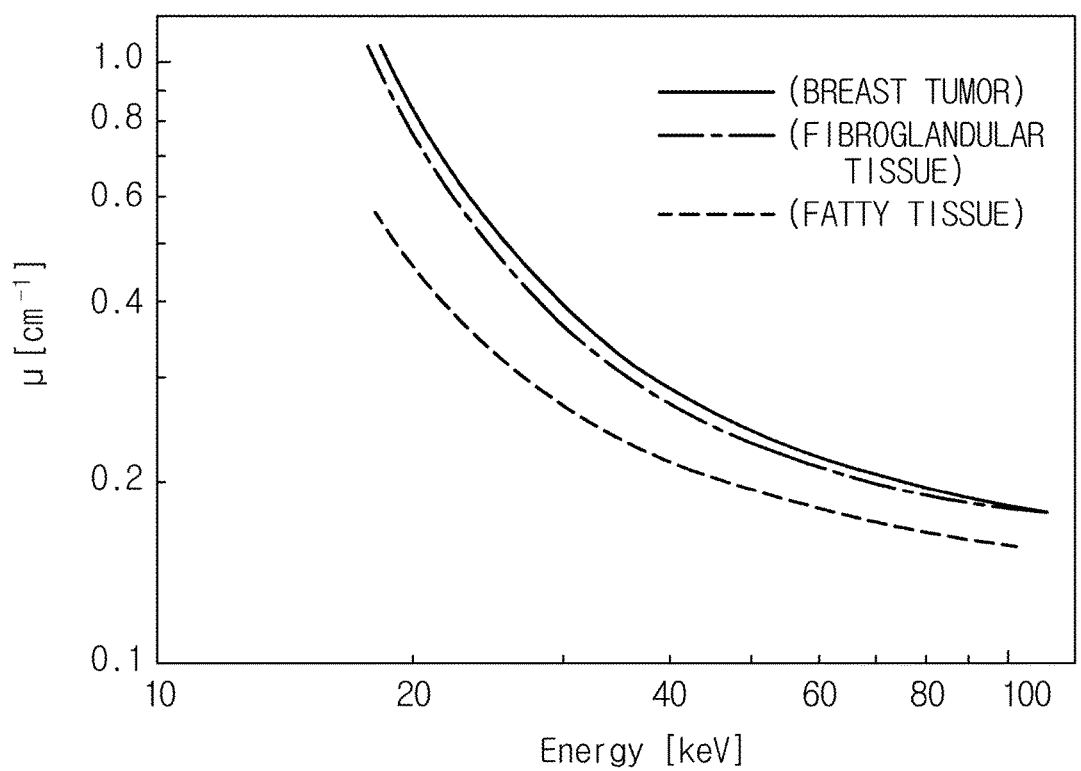
FIG. 4 is a graph showing X-ray attenuation coefficients of parts constituting a breast.

FIG. 3 is a schematic view illustrating an internal structure of a breast, and FIG. 4 is a graph showing X-ray attenuation coefficients of parts constituting a breast.

Referring to FIG. 3, tissues of the breast 30 include a fibrous tissue 31 which covers an overall breast and maintains a form of the breast 30, a fatty tissue 32 distributed throughout the breast 30, a glandular tissue 33 to produce breast milk, a connective tissue 34 which functions as a duct for transporting breast milk. The glandular tissue 33 and the connective tissue 34 which are related to production and supply of the breast milk are referred to as a fibroglandular tissue.

An attenuation coefficient of the breast 30 is data indicating a degree of attenuation of the transmitted X-rays. Since each material constituting the internal structure of the object has a different attenuation coefficient, an image of the internal structure of the object may be obtained by transmitting X-rays through the object.

Since the breast 30 comprises only soft tissues, a difference in the attenuation coefficient among materials constituting the breast 30 may not be larger, as shown in FIG. 4. Therefore, to acquire a sharper X-ray image, X-rays in a lower energy band, which produce a relatively large difference in the attenuation coefficient among constituent materials, may be emitted. To emit X-rays in a lower energy band, the tube voltage supplied to the X-ray tube 111 may be decreased. For example, in a case where the object 30 is a breast, tube voltage of about 30 kVp may be supplied to emit X-rays having a maximum energy of about 30 keV.

Since an X-ray in the lower energy band has a lower transmittance with respect to the materials constituting the breast 30, the breast 30 needs to be compressed using the compression paddle 131 to decrease a thickness of the breast 30 to obtain a sharper X-ray image of the breast 30. In addition, when the thickness of the breast 30 decreases, the X-ray exposure dose may also be reduced. In addition, when the breast 30 is compressed, the constituent materials of the breast 30 may not overlap each other in a direction of emission of X-rays but spread out, and accordingly, image quality may be improved.

Accordingly, in capturing an X-ray image of the breast 30, compression of the breast 30 is a very important control factor.

Figure 5:
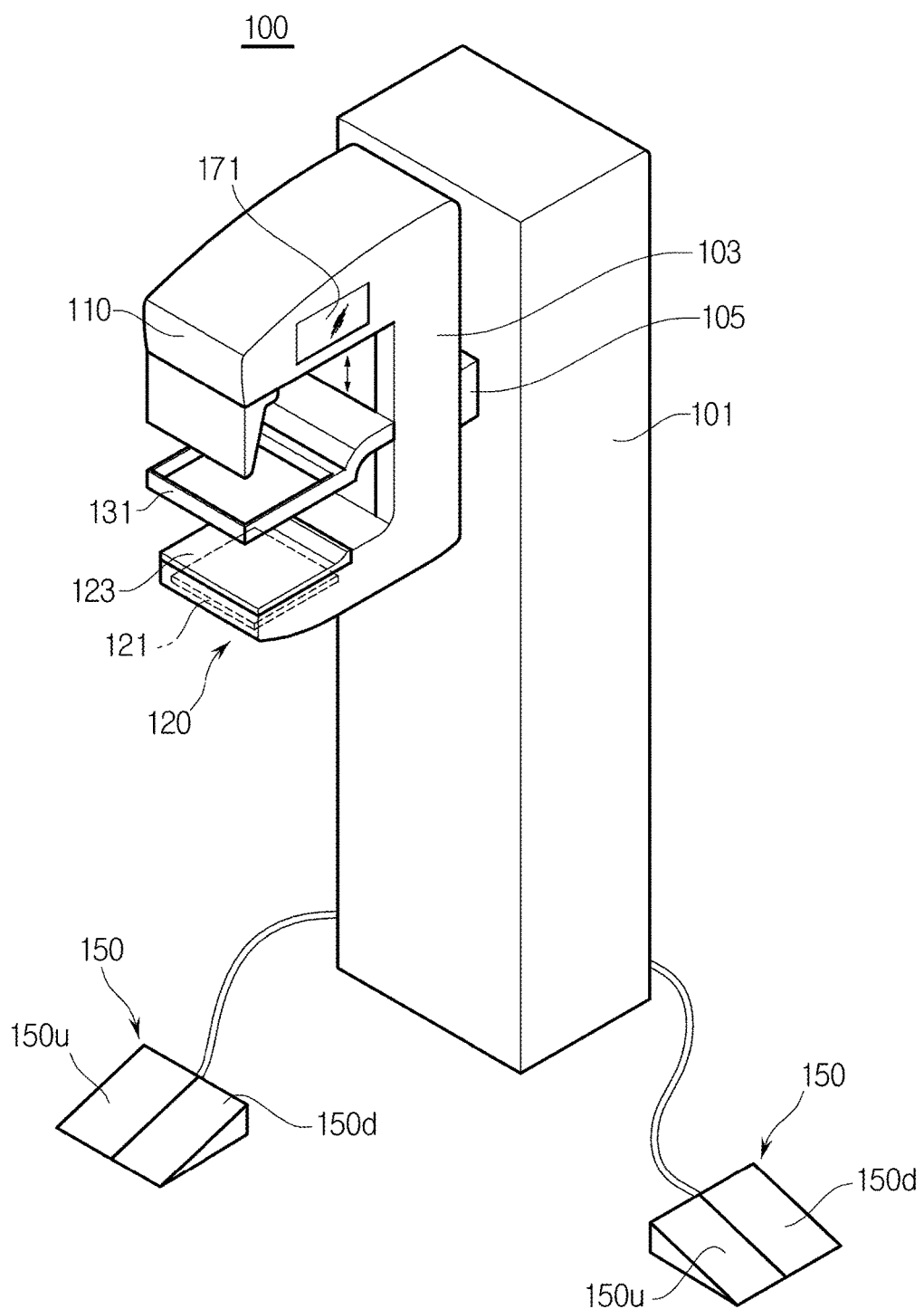
FIG. 5 is a view showing an external appearance of an X-ray imaging apparatus according to an exemplary embodiment.

FIG. 5 is a view showing an external appearance of an X-ray imaging apparatus according to an exemplary embodiment.

The X-ray imaging apparatus 100 is used to capture an X-ray image of the object, i.e., the breast 30. In an exemplary embodiment, the object indicates an examined portion of a subject for diagnosis using the X-ray imaging apparatus 100, and the examined portion may be a living body including a human body. Due to properties of the breast 30, the X-ray imaging apparatus 100 to capture an image of the breast 30 has an element different from those of other typical X-ray imaging apparatuses. For example, the X-ray imaging apparatus 100 for imaging of the breast is the compression paddle 131 to compress the breast 30. Hereinafter, a structure and an operation of the X-ray imaging apparatus 100 will be described in detail with reference to FIG. 5.

The X-ray source 110 and the detector assembly 120 are connected to a frame 103 to face each other. The frame 103 may be connected to a body 101 through an arm 105. The arm 105 may vertically move according to with a height of the subject or may rotate by a certain angle such that the X-ray imaging apparatus 100 acquires a tomogram or a three-dimensional image of the object.

To capture an X-ray image of the object, i.e., the breast, the breast is positioned between the X-ray source 110 and the detector assembly 120 such that X-rays emitted from the X-ray source 110 and transmitted through the breast are detectable by the detector assembly 120.

The detector assembly 120 also functions as a support or a table to support the breast. The detector assembly 120 is also referred to as a Bucky. Specifically, the detector assembly 120 includes an X-ray detector 121 provided therein. The detector assembly 120 further includes a breast contact portion 123 to contact the breast. The breast contact portion 123 may comprise a material with a higher X-ray transmittance. For example, the breast contact portion 123 may comprise a carbon sheet.

When the breast is placed on the breast contact portion 123, a user may manipulate the paddle manipulator 150 to vertically move the compression paddle 131.

The user may input a command for moving the compression paddle 131 through the paddle manipulator 150. The paddle manipulator 150 may transmit a control signal to the paddle driver 133 (see FIG. 1) to control movement of the compression paddle 131. For example, the paddle driver 133 may include a motor and a drive. The paddle driver 133 may further include a structure such as a gear to transfer a driving force of the motor to the compression paddle 131.

For example, the paddle manipulator 150 may be realized as a foot button or a foot pedal, as shown in FIG. 5. When the paddle manipulator 150 is realized as a the foot button, the user may effectively compress the breast by adjusting a position of the breast of the subject by a user's hand and adjusting movement of the compression paddle 131 by a user's foot.

The paddle manipulator 150 may include an up button 150*u* to move the compression paddle 131 upward and a down button 150*d* to move the compression paddle 131 downward. The paddle manipulator 150 may be provided to correspond to left and right sides of the body 101, respectively, to allow the user to move the compression paddle 131 according to manipulation from the left and right sides of the body 101. Although the paddle manipulator 150 realized as the foot button is illustrated in FIG. 5, exemplary embodiments are not limited thereto.

Figure 6A:
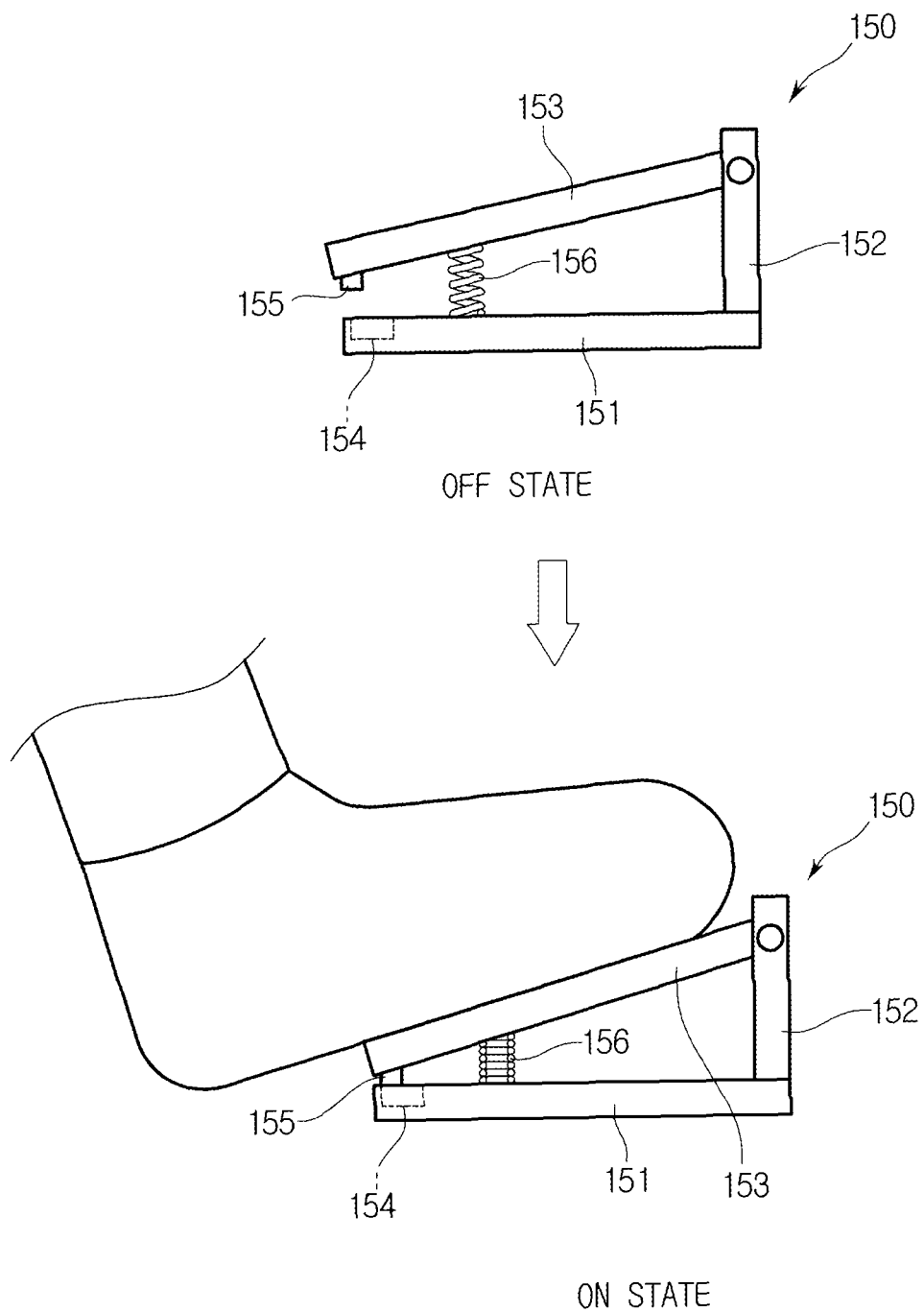
FIGS. 6A and 6B are side views showing a structure of a paddle manipulator according to exemplary embodiments.
Figure 6B:
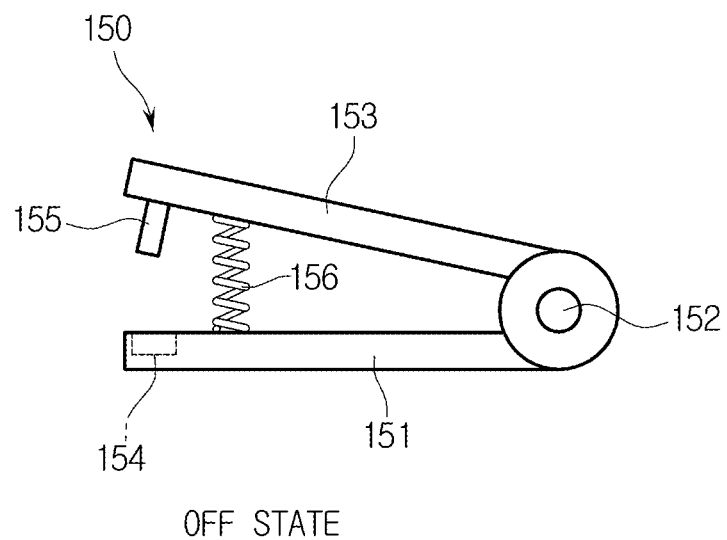
Figure 6B:
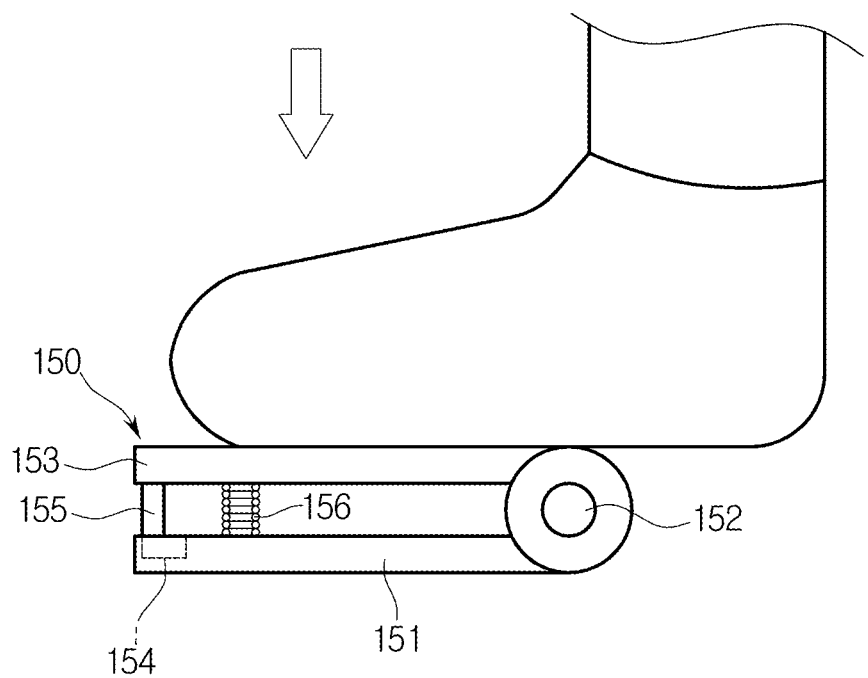

FIGS. 6A and 6B are side views showing a structure of a paddle manipulator according to exemplary embodiments. In FIGS. 6A and 6B, the paddle manipulator 150 is shown as a foot button, and a structure to which pressure is supplied is omitted.

Referring to FIGS. 6A and 6B, the paddle manipulator 150 includes a lower plate 151 having a switch 154 mounted therein, and an upper plate 153 vertically moved by external force. An end portion of the upper plate 153 may be pivotally mounted to a support 152, and an opposite end portion of the upper plate 153 may be provided with a protrusion 155 to press the switch 154 of the lower plate 151.

An elastic member 156 may be installed between the upper plate 153 and the lower plate 151 such that the protrusion 155 does not press the switch 154 when external force is not applied to the upper plate 153 and presses the switch 154 when the external force is applied to the upper plate 153.

When the protrusion 155 presses the switch 154, the switch 154 is turned on. When the protrusion 155 does not press the switch 154, the switch 154 is turned off. That is, a state in which external force is not applied to the upper plate 153, i.e., a state in which the user does not press the paddle manipulator 150 is an OFF state of the switch 154. Also, a state in which external force is applied to the upper plate 153, i.e., a state in which the user presses the paddle manipulator 150, is an ON state of the switch 154. In an alternative embodiment, the protrusion 155 may be omitted, and an end portion of the upper plate 153 may directly contact the switch 154 when external force is applied thereto.

When the user's foot pushes the paddle manipulator 150 to turn on the switch 154, an ON signal is transmitted to the paddle driver 133 and the paddle driver 133 provides driving force to move the compression paddle 131. For example, when the user presses the down button 150d, the compression paddle 131 moves downward. When the user presses the up button 150u, the compression paddle 131 may move upward. Herein, a moving speed of the compression paddle 131 may be preset to a certain speed.

During when the user continues to press the paddle manipulator 150, the compression paddle 131 continues to move. When the user stops pressing the paddle manipulator 150, the compression paddle 131 also stops moving. Accordingly, by controlling pressing and stopping the paddle manipulator 150, the user may finely adjust movement of the compression paddle 131.

Structures and operations illustrated in FIGS. 6A and 6B are similar to each other, but positions of the protrusion 155 of the paddle manipulator 150 are different. Accordingly, in a case where the paddle manipulator 150 has a structure shown in FIG. 6A, the user may control the paddle manipulator 150 by pressing one of the two end portions of the upper plate 153 which is closer to the user. In a case where the paddle manipulator 150 has a structure shown in FIG. 6B, the user may control the paddle manipulator 150 by pressing a more distal end portion of the two end portions. It should be noted that there is no limit as to structures of the paddle manipulator 150 applicable to the X-ray imaging apparatus 100.

When the breast is compressed by the compression paddle 131, the degree-of-compression sensor 141 measures a degree of compression of the breast and displays the same on a display 171 (see FIG. 5). The user may check the degree of compression displayed on the display 171 and may adjust the degree of compression of the breast based on the displayed information. However, it may be difficult to understand the degree of compression experienced by the subject solely depending on the information displayed on the display 171. In addition, while the user positions the breast, the use may fail to view the display 171. Accordingly, the degree-of-compression sensor 141 also transfers the measured degree of compression to the pressure controller 143 such that a corresponding pressure is supplied to the paddle manipulator 150.

Figure 7:
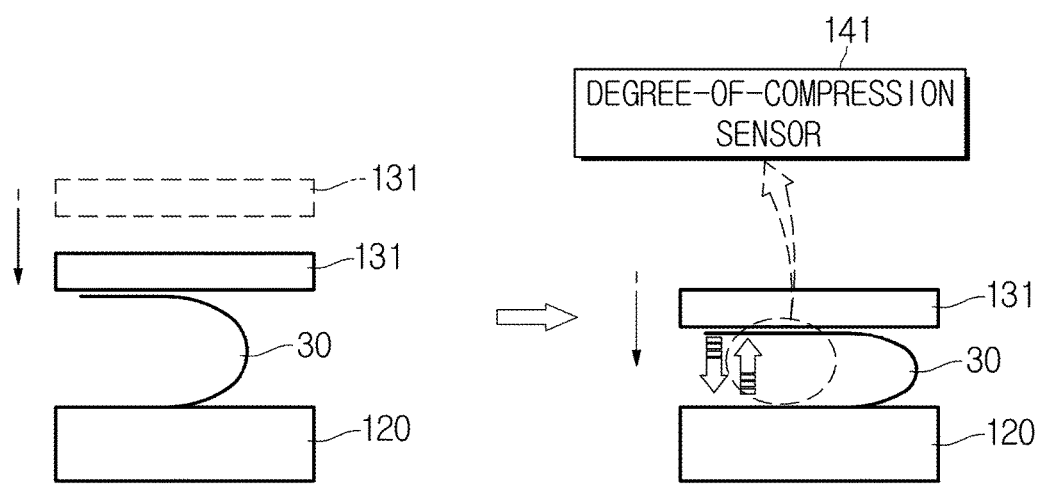
FIG. 7 is a schematic view illustrating measurement of a degree of compression according to an exemplary embodiment.

FIG. 7 is a schematic view illustrating measurement of a degree of compression according to an exemplary embodiment.

As shown in FIG. 7, when the breast 30 is placed on an upper portion of the detector assembly 120 and the compression paddle 131 begins to compress the breast 30 by moving downward, the breast 30 is compressed by force applied by the compression paddle 131, and a reaction force of substantially the same magnitude is applied to the compression paddle 131 by the breast 30. Accordingly, by mounting the degree-of-compression sensor 141 to the compression paddle 131 and measuring the force applied by the compression paddle 131 using the degree-of-compression sensor 141, the degree of compression of the breast 30 may be measured.

The measured degree of compression may be represented by force or pressure. Accordingly, the degree-of-compression sensor 141 may be realized as a force sensor or a pressure sensor. For example, in a case where force applied by the compression paddle 131 is measured by the degree-of-compression sensor 141 based on elastic deformation of the breast, an amount of elastic deformation may be mechanically measured using a dial gauge or a micrometer, or optically measured using light wave interference or Moiré pattern, or electrically measured using a strain gauge, a differential transformer or a capacitor. Alternatively, force may be measured based on a physical effect such as a piezoelectric effect with a crystal or barium titanate or the magnetostriction effect with a magnetostrictive tube or a magnetic cell.

Since pressure is defined force per unit area, the pressure controller 143 may transform the degree of compression transmitted from the degree-of-compression sensor 141 into a desired scale, regardless of a type of the degree of compression, and use a value of the desired scale to control pressure supplied to the paddle manipulator 150.

The degree-of-compression sensor 141 may measure the degree of compression of the breast in real time or at regular intervals.

Figure 8:
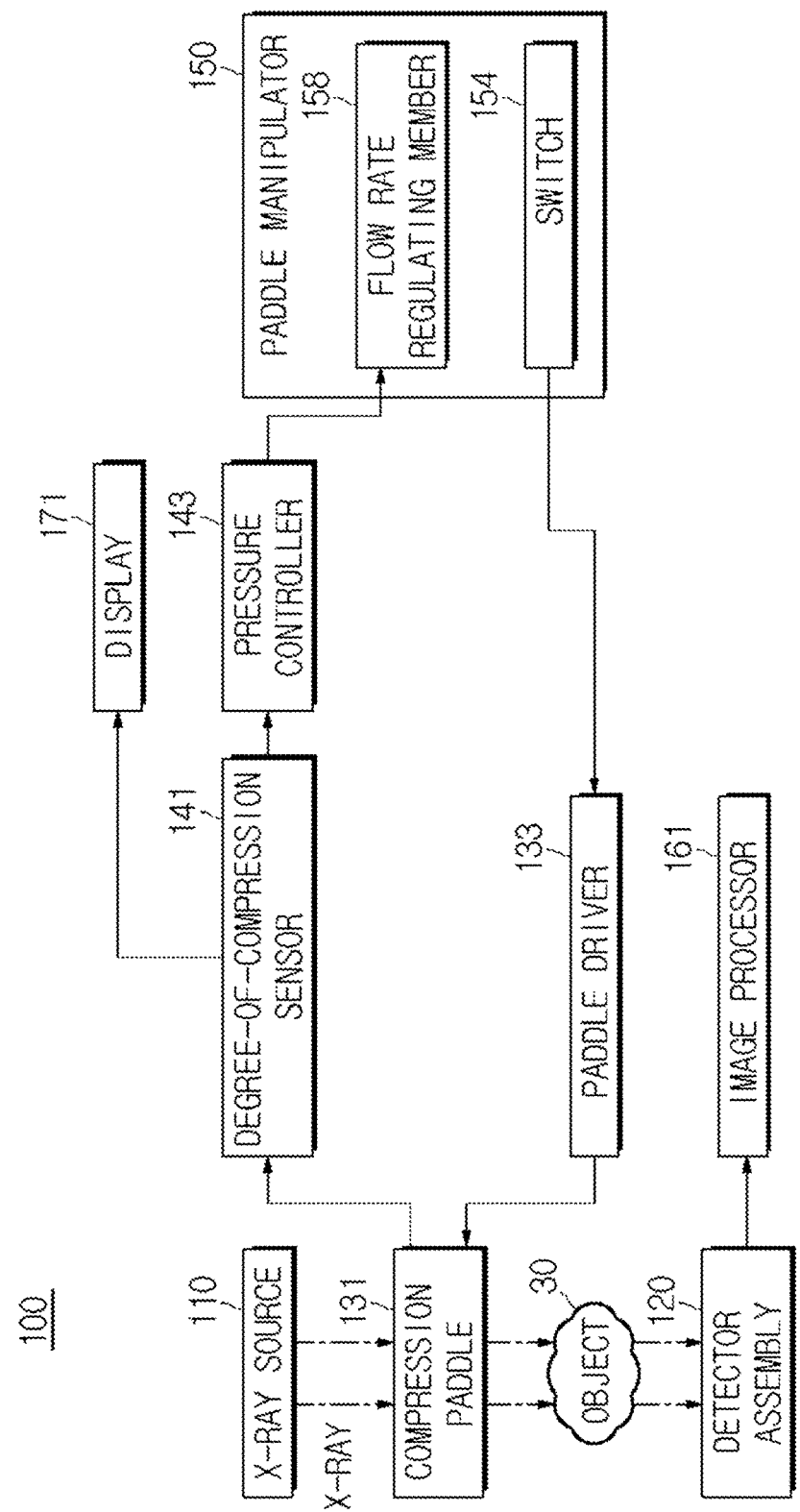
FIG. 8 is a detailed control block diagram illustrating an X-ray imaging apparatus according to an exemplary embodiment.
Figure 9A:
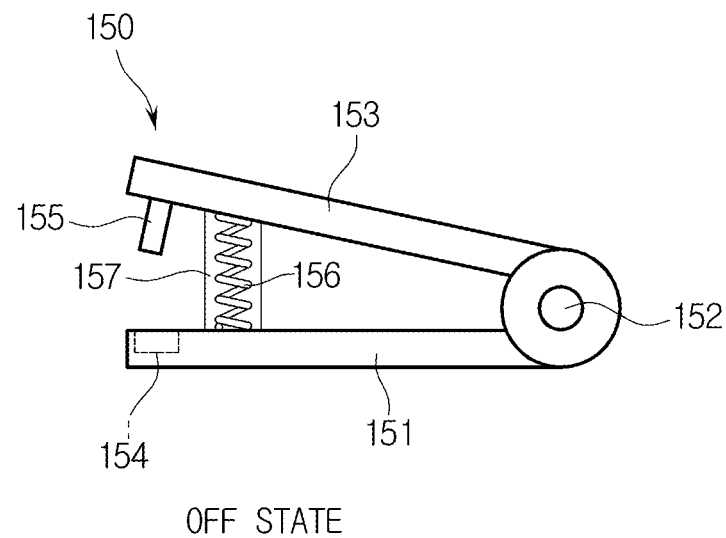
FIGS. 9A to 9C are side views showing a structure of a paddle manipulator according to various exemplary embodiments.
Figure 9A:
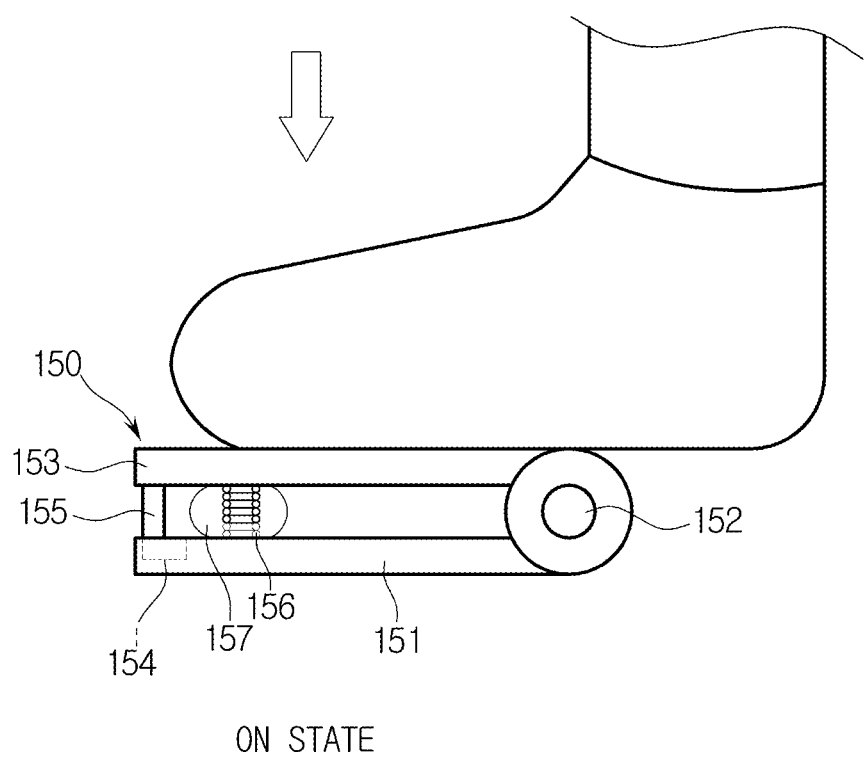
Figure 9B:
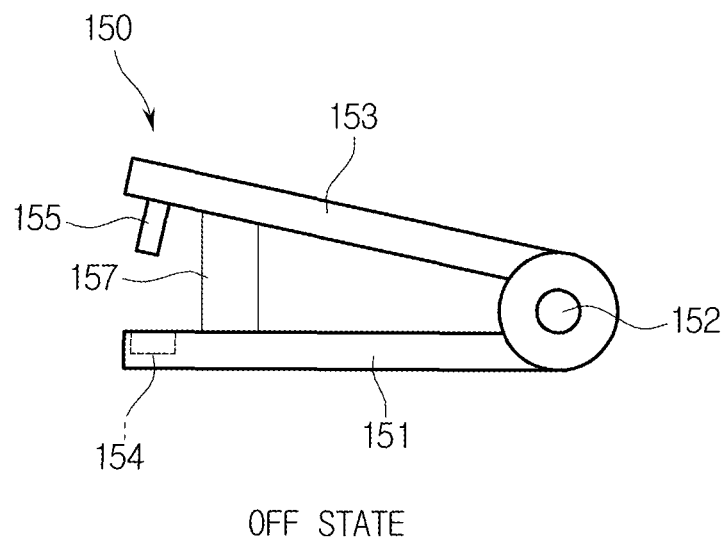
Figure 9B:
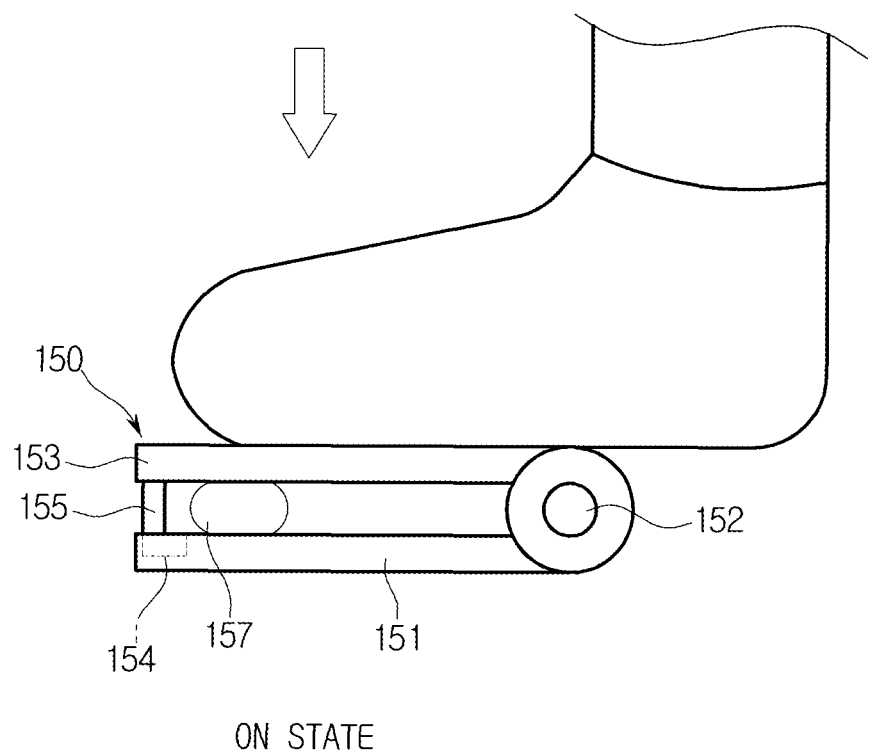
Figure 9C:
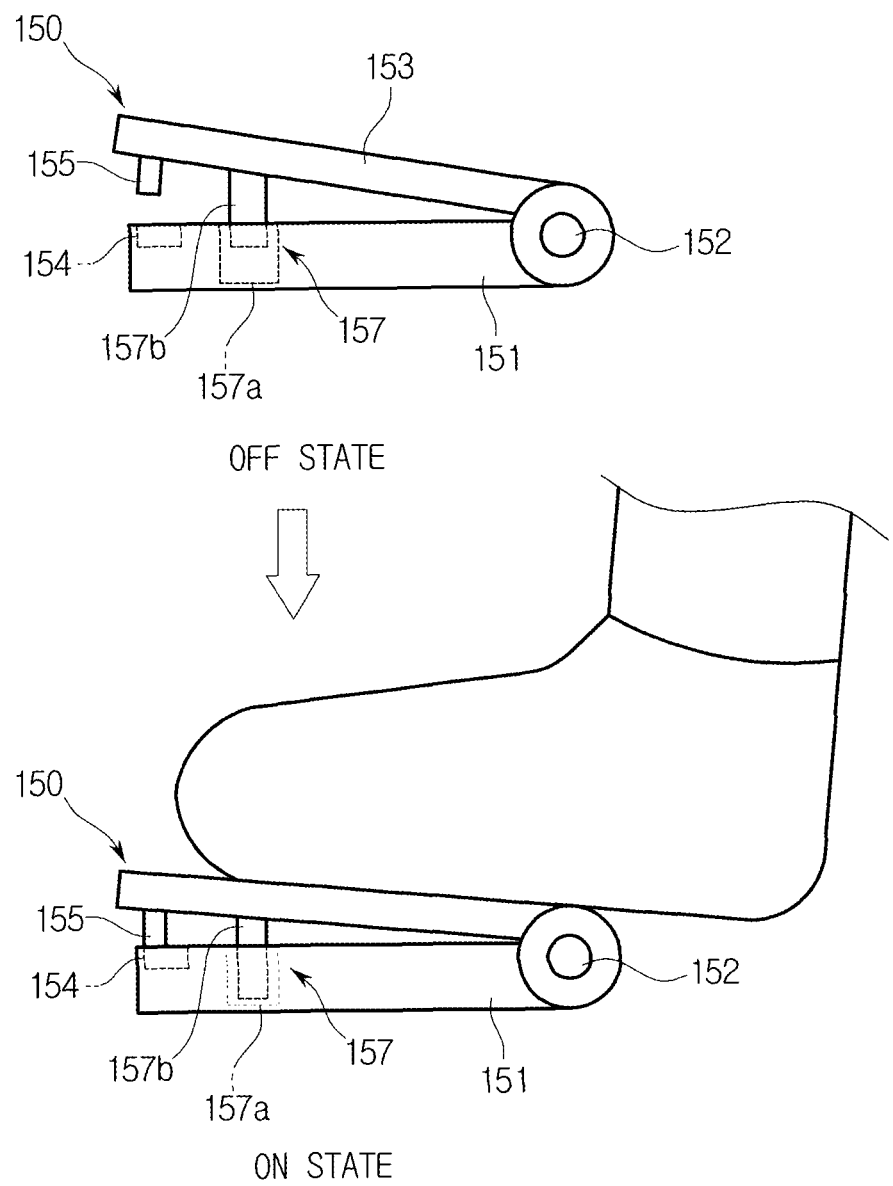

FIG. 8 is a detailed control block diagram illustrating an X-ray imaging apparatus according to an exemplary embodiment. FIGS. 9A to 9C are side views showing a structure of a paddle manipulator according to various exemplary embodiments.

In an exemplary embodiment, the paddle manipulator 150 may provide hydraulic pressure as the degree of compression of the breast. That is, the degree of compression of the breast may be provided in a form of hydraulic pressure. Referring to FIG. 8, the paddle manipulator 150 may include a flow rate regulating member 158 and a switch 154. When a degree of compression of the breast is measured and transmitted to the pressure controller 143 by the degree-ofcompression sensor 141, the pressure controller 143 controls the flow rate regulating member 158 of the paddle manipulator 150 to supply hydraulic pressure corresponding to the degree of compression of the breast to the paddle manipulator 150.

The pressure controller 143 may include one or more hardware and/or software components. For example, the pressure controller 143 may include one or more of an integrated circuitry, a dedicated circuit, firmware, and/or a processor such as a central processing unit (CPU) which executes software programs stored in a storage, e.g., a memory.

Hereinafter, a structure of the paddle manipulator 150 to receive pressure according to various exemplary embodiments will be described with reference to FIGS. 9A to 9C.

According to an exemplary embodiment illustrated in FIG. 9A, the paddle manipulator 150 may further include, in addition to a structure illustrated in FIG. 6B, a fluid accommodation portion 157 to accommodate fluid therein. The fluid may include liquid or gas. Accordingly, liquid or gas may be accommodated in the fluid accommodation portion 157. For example, the liquid may be oil and the gas may be air. Although not shown in FIG. 9A, the flow rate regulating member 158 may be arranged at an outer or inner portion of the fluid accommodation portion 157 to adjust an amount of fluid accommodated in the fluid accommodation portion 157. For example, the flow rate regulating member 158 may be realized as a valve, a pump, or a fan.

In an exemplary embodiment, the pressure controller 143 may control the flow rate regulating member 158 such that pressure of the fluid accommodated in the fluid accommodation portion 157 corresponds to the degree of compression of the breast. The fluid accommodation portion 157 may comprise an elastic material such as rubber such that the user may feel the pressure of the accommodated fluid when external force is applied thereto, and the fluid accommodation portion 157 may return to an original shape thereof when external force applied thereto is removed.

As shown in FIG. 9A, when the breast is compressed, fluid having pressure corresponding to the degree of compression of the breast may be introduced into the fluid accommodation portion 157. When the user steps on and pushes the paddle manipulator 150 to turn on the switch 154, the user may feel the pressure corresponding to the degree of compression of the breast. Accordingly, to further push down the fluid accommodation portion 157 to cause the protrusion 155 to contact the switch 154, the user may need to apply force greater than force corresponding to the pressure of the fluid accommodation portion 157. Through this operation, the user may feel the degree of compression of the breast.

According to another exemplary embodiment shown in FIG. 9B, the elastic member 156 may be omitted from the paddle manipulator 150 of FIG. 9A. In this case, in an initial state, fluid with a certain pressure is accommodated in the fluid accommodation portion 157 having elasticity to serve as the elastic member 156. When the user begins to compress the breast, the fluid having the pressure corresponding to the degree of compression of the breast may be further introduced into the fluid accommodation portion 157. Similarly, the user needs to apply force increased from force greater than force corresponding to the pressure of the fluid accommodation portion 157 to cause the protrusion 155 to contact the switch 154. Thereby, the user may indirectly feel the degree of compression of the breast.

According to a further exemplary embodiment shown in FIG. 9C, the fluid accommodation portion 157 may be realized as a gas spring or a hydraulic cylinder. Since structures of the gas spring and the hydraulic cylinder are widely known, a detailed description thereof will be omitted, and only elements related to transfer of pressure to the paddle manipulator 150 will be described.

The fluid accommodation portion 157 may include a cylinder housing and a piston rod 157b. The cylinder housing 157a is filled with gas or liquid, e.g., air or oil, having pressure corresponding to the degree of compression of the breast. When the user pushes the protrusion 155 to cause the switch 154 to contact the upper plate 153, the piston rod 157b may transfer force corresponding to the degree of compression of the breast to the user and enter into the cylinder housing 157a. In determining an amount of the gas or the liquid, e.g., air or oil, to fill the cylinder housing 157a, an area of the piston rod 157b may also be considered.

Structures of the paddle manipulator 150 illustrated in FIGS. 9A to 9C are only examples and it should be noted that any structure for receiving pressure corresponding to the degree of compression of the breast and transferring the same to the user may be applicable to the paddle manipulator 150.

Figure 10:
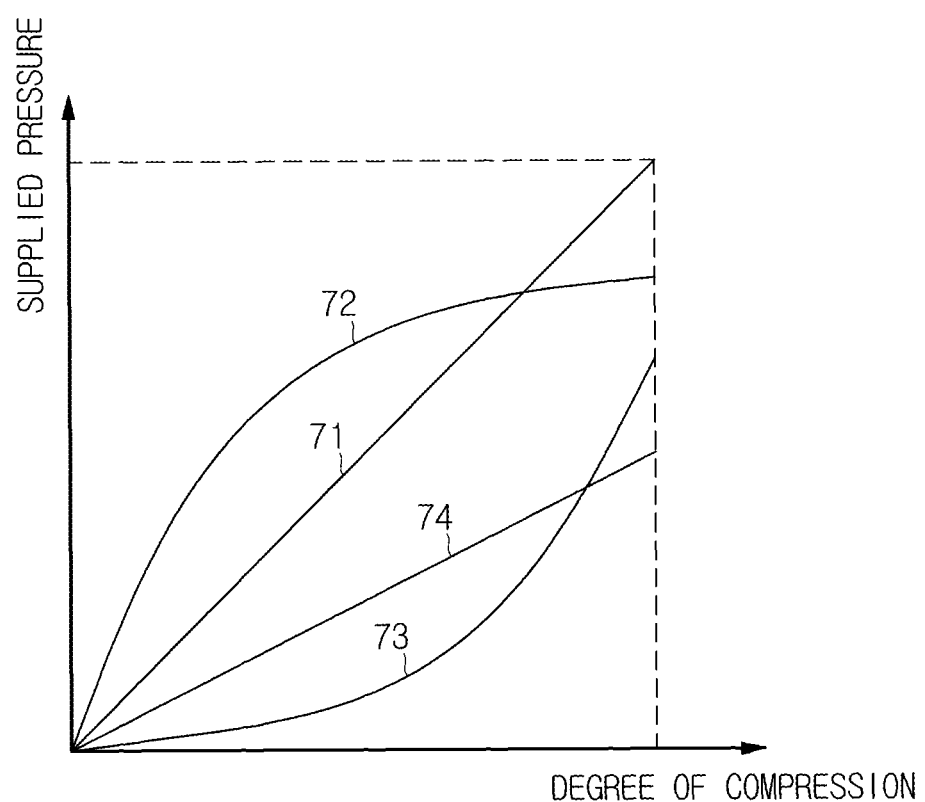
FIG. 10 are graphs showing a relationship between a measured degree of compression and pressure provided to a paddle manipulator according to various exemplary embodiments.

As described above, the pressure controller 143 supplies pressure corresponding to the degree of compression of the breast to the paddle manipulator 150. FIG. 10 are graphs showing a relationship between a measured degree of compression and pressure supplied to a paddle manipulator according to various exemplary embodiments. Hereinafter, pressure corresponding to the degree of compression of the breast will be described in detail with reference to FIG. 10.

A magnitude of pressure supplied to the paddle manipulator 150 may be varied depending on embodiments. For example, the pressure controller 143 may supply pressure which is linearly proportional to the degree of compression of the breast to the paddle manipulator 150. In this case, a proportionality constant between the degree of compression of the breast and the pressure supplied to the paddle manipulator 150 may be appropriately adjusted.

In an exemplary embodiment, the pressure controller 143 may have a proportionality constant equal to 1, as shown in an exemplary graph 71. That is, the pressure controller 143 may supply pressure having the same magnitude as the degree of compression to the paddle manipulator 150 to allow the user to feel the actual pressure applied to the breast. In this case, compression may be performed in consideration of pressure felt by the subject.

Alternatively, the pressure controller 143 may have a proportionality constant greater than 0 and less than 1, as shown in an exemplary graph 74. In this case, the user may be allowed to manipulate the paddle manipulator 150 without applying excessive force when the degree of compression of the breast increases. Accordingly, enhanced convenience of manipulation may be provided to the user.

Alternatively, the pressure controller 143 may supply pressure nonlinearly proportional to the degree of compression of the breast to the paddle manipulator 150.

For example, by increasing an increase rate of pressure supplied to the paddle manipulator 150 as the degree of compression of the breast increases, as shown in an exemplary graph i 73, sensitivity of the paddle manipulator 150 may be reduced and safety may be improved in response to an increase of the degree of compression of the breast. That is, as the degree of compression of the breast increases, more force is needed to manipulate the paddle manipulator 150. Accordingly, sensitivity of the paddle manipulator 150 is reduced and thus safety may be improved.

In another example, the pressure controller 143 may reduce the increase rate of pressure supplied to the paddle manipulator 150 as the degree of compression of the breast increases, as shown in an exemplary graph 72. Therefore, enhanced convenience of manipulation may be provided to the user.

The pressure corresponding to the degree of compression of the breast supplied to the paddle manipulator 150 may vary depending on setting of the pressure controller 143. The relationship between the degree of compression of the breast and the pressure supplied to the paddle manipulator 150 may be set in various ways to be used by the pressure controller 143.

The degree of compression, based upon which a control operation by the pressure controller 143 is performed, may be represented by pressure or force. For example, in the case of the graph 71, when the degree of compression is 120N, pressure supplied to the paddle manipulator 150, i.e., pressure corresponding to the degree of compression, may be pressure that causes substantially the same effect of applying the force of 120N to the paddle manipulator 150. In other words, the pressure which may produce 120N as reaction force may be applied to the user who applies external force to the paddle manipulator 150.

In the above exemplary embodiments of the X-ray imaging apparatus 100, the paddle manipulator 150 is described as the foot button. However, exemplary embodiments are not limited thereto. For example, the paddle manipulator 150 may alternatively be realized as a button which may be manipulated by the user's hand.

Figure 11A:
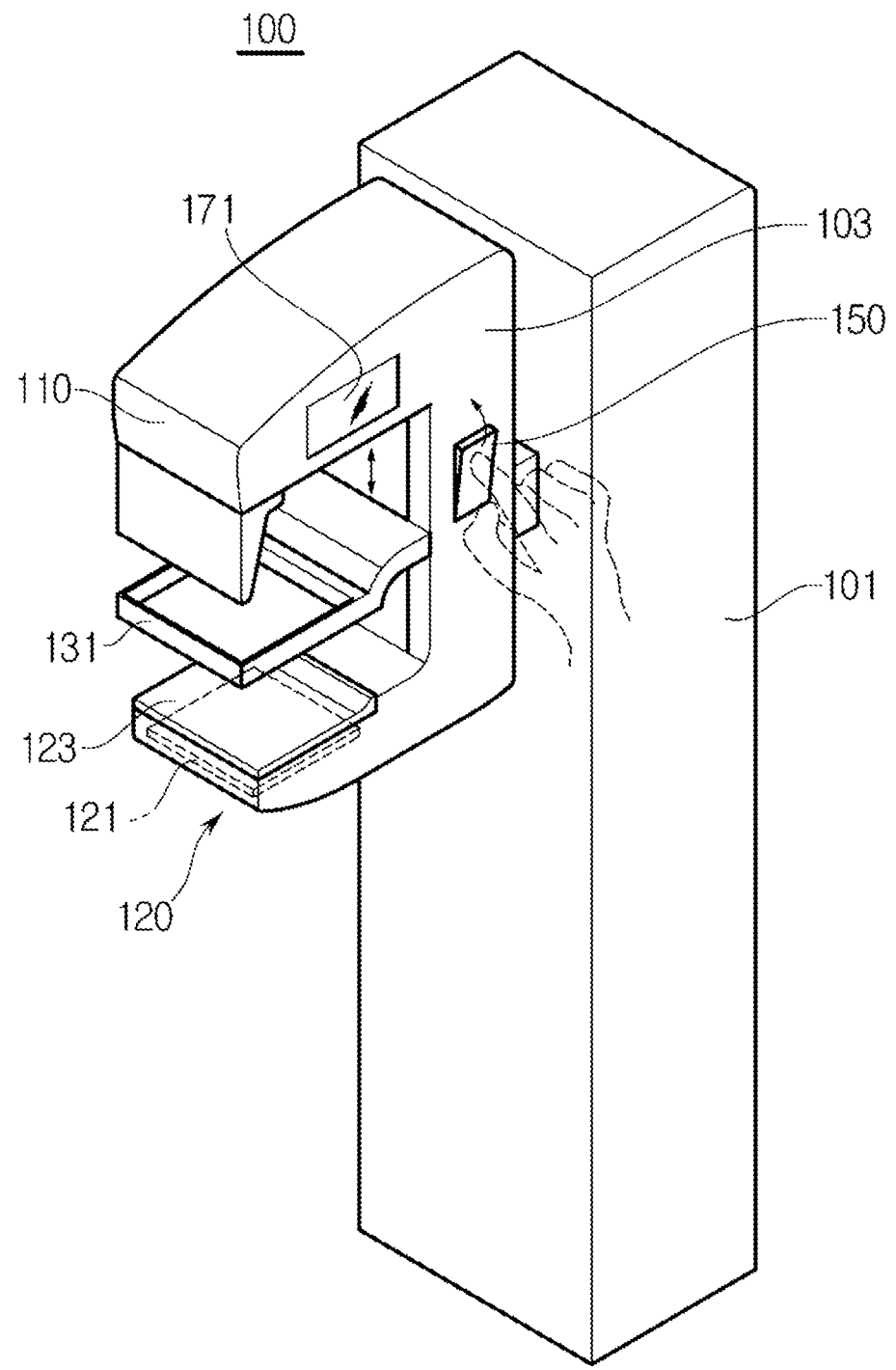
FIGS. 11A and 11B show examples of a paddle manipulator which is manually operated.
Figure 11B:
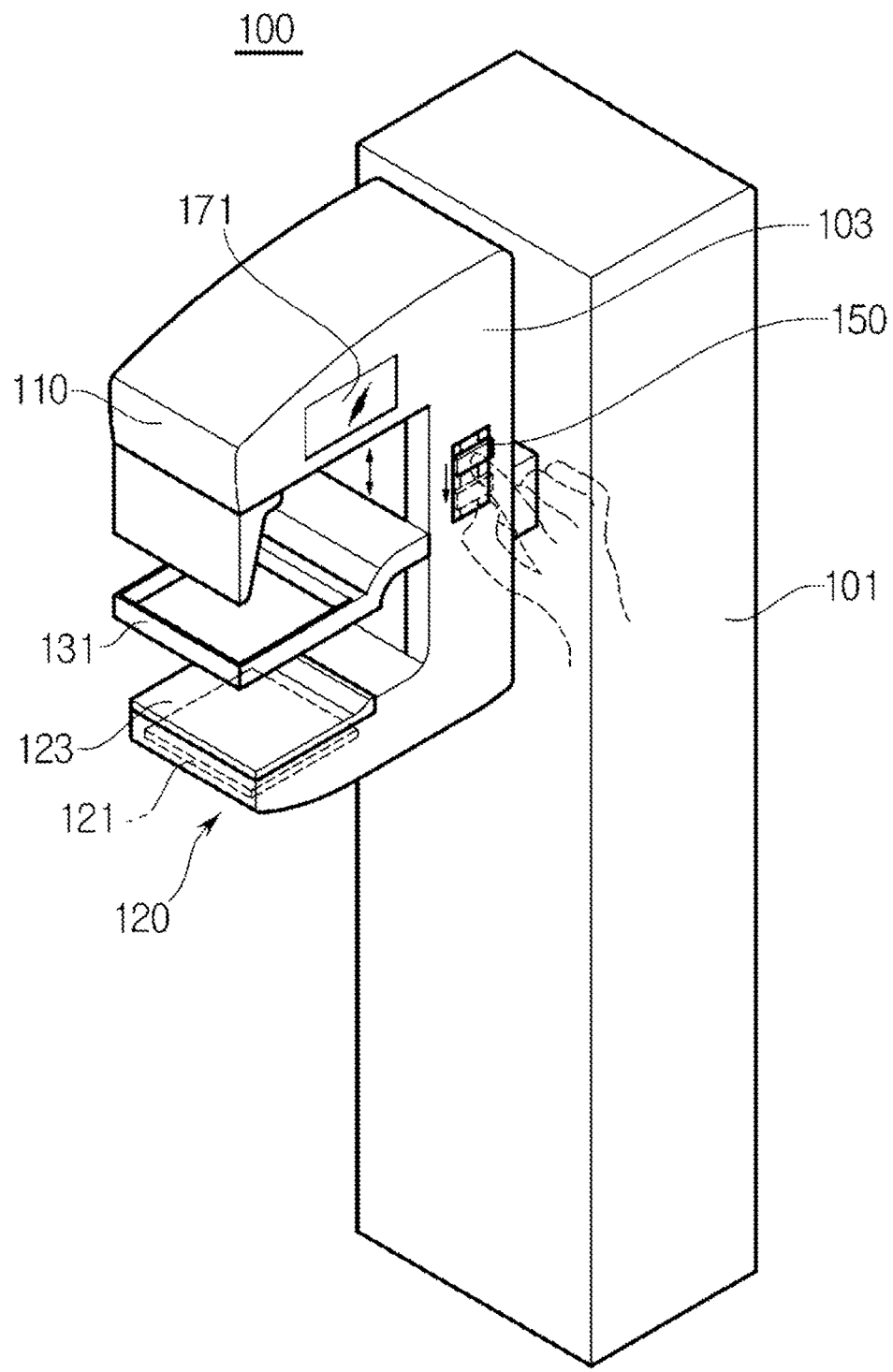

FIGS. 11A and 11B show examples of a paddle manipulator which is manually operated.

Referring to an exemplary embodiment shown in FIG. 11A, the paddle manipulator 150 may be provided on a surface of the frame 103. Except that the paddle manipulator 150 is mounted to the frame 103 and manually manipulated by the user, the structure of the paddle manipulator 150 may be substantially the same or similar to those shown in FIGS. 9A to 9C. That is, a fluid accommodation portion may be provided in the paddle manipulator 150 such that an amount of fluid accommodated in the fluid accommodation portion may increase as the degree of compression of the breast increases.

Referring to another exemplary embodiment shown in FIG. 11B, the paddle manipulator 150 may be realized as a lever which is vertically moved. In this case, except for a direction in which the paddle manipulator 150 is pressed, a structure and an operation of the paddle manipulator 150 may be substantially the same or similar to those of the paddle manipulator shown in FIGS. 9A to 9C. Specifically, while the paddle manipulator 150 of FIG. 11A needs to be pressed to manipulate the compression paddle 131, the paddle manipulator 150 of FIG. 11B needs to move vertically (i.e., in an up-down direction) to manipulate the compression paddle 131.

In a case where the paddle manipulator 150 is manually manipulated by the user, a manual paddle manipulator to move the compression paddle 131 upward and a manual paddle manipulator to move the compression paddle 131 downward may be respectively provided.

According to the above exemplary embodiments, when the user compresses the breast with the compression paddle 131 by manipulating the paddle manipulator 150, the degree of compression of the breast is measured in real time or at regular time intervals and fed back to the user. A feedback of the degree of compression of the breast may be provided by numerically displaying the degree of compression of the breast on the display 171 and providing pressure corresponding to the degree of compression of the breast to the paddle manipulator 150. Since the user recognizes the degree of compression through numerical information, and at the same time feels the degree of compression of the breast through a controller 150, more accurate and safer compression of the breast may be implemented.

When compression of the breast is completed, the X-ray source 110 emits X-rays, and the X-ray detector 121 detects the X-rays transmitted through the breast to capture an X-ray image of the breast. For example, the X-ray imaging apparatus 100 may be provided with a compression completion button (not shown) to determine completion of compression of the breast when the compression completion button is pressed. Also, for example, the X-ray imaging apparatus 100 may be provided with a compression start button (not shown) to determine compression of the breast when the X-ray imaging start button is pressed.

Hereinafter, a control method for an X-ray imaging apparatus according to an exemplary embodiment will be described.

Figure 12:
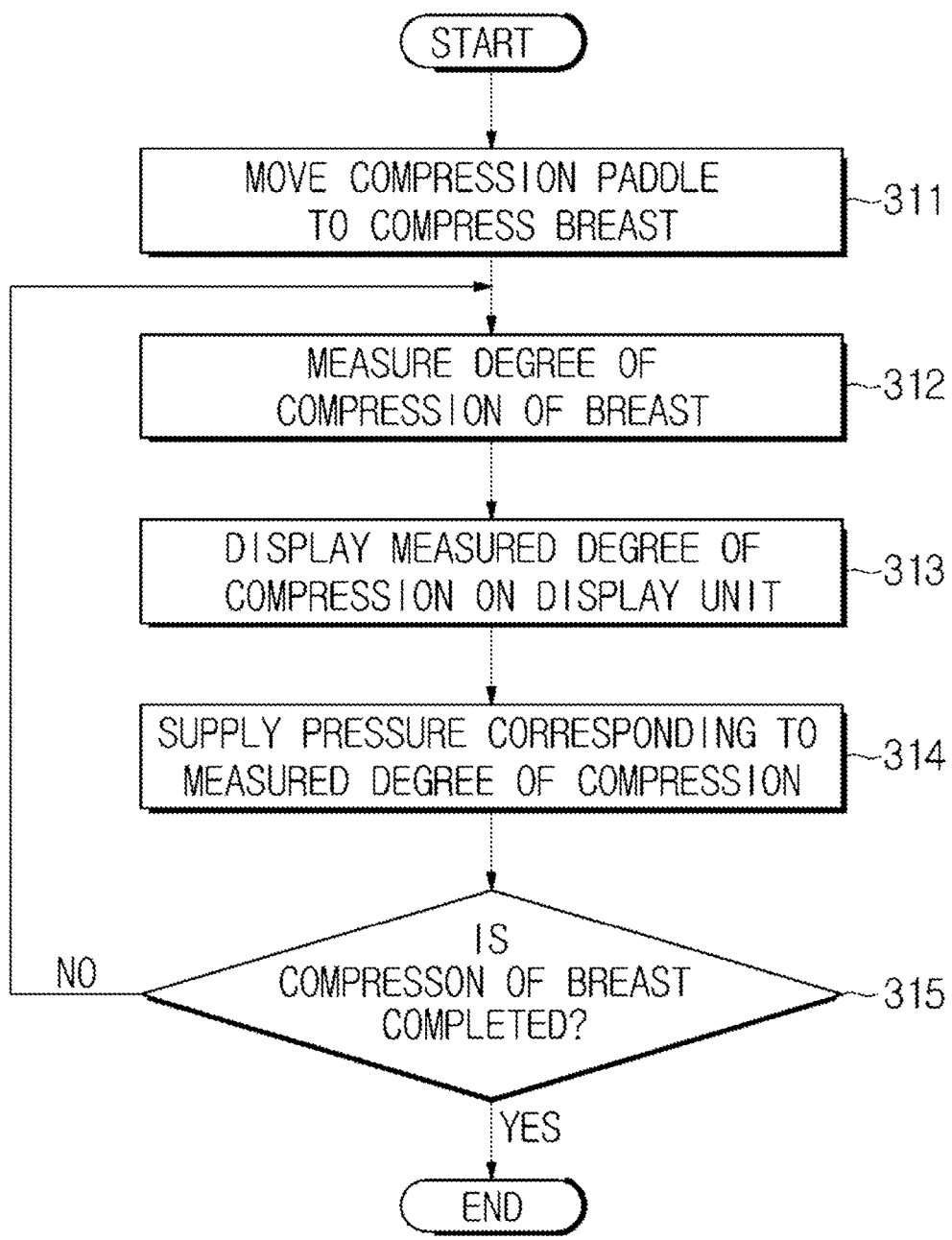
FIG. 12 is a flowchart illustrating a control method for an X-ray imaging apparatus according to an exemplary embodiment.

FIG. 12 is a flowchart illustrating a control method of an X-ray imaging apparatus according to an exemplary embodiment. A control method of an X-ray imaging apparatus according to an exemplary embodiment may apply to the X-ray imaging apparatus 100 according to the above exemplary embodiments may be applied.

First, the breast may be positioned on the detector assembly 120, and the breast may be compressed by moving the compression paddle (311). The user may manipulate the paddle manipulator 150 to move the compression paddle 131. For example, the paddle manipulator 150 may be realized as a foot button or a foot pedal which is positioned on the ground on which the X-ray imaging apparatus 100 is placed to be manipulated by the user's foot. Alternatively, the paddle manipulator may be provided on one surface of the X-ray imaging apparatus 100 such as the frame 103 or the body 101 to be manipulated by the user's hand. The paddle manipulator 150 may have a structure as described above with reference to FIGS. 9A to 9C, 11A and 11B.

Next, the degree of compression of the breast may be measured (312). The degree of compression of the breast may be measured in the form of force or pressure by the degree-of-compression sensor 141 mounted on the compression paddle 131. In addition, the degree of compression of the breast may be measured in real time or at regular intervals.

The measured degree of compression may be displayed on a display (313). The display 171 may be mounted to a surface of, for example, one of the X-ray source 110, the frame 103, and the detector assembly 120. For example, the display 171 may be positioned such that the user who adjusts the position of the breast may easily check the position of the breast. The degree of compression displayed on the display 171 may be updated in real time or at regular time intervals.

Next, a pressure corresponding to the measured degree of compression may be supplied to the paddle manipulator 150 (314). To this end, the paddle manipulator 150 may be provided with the fluid accommodation portion 157 to accommodate fluid having pressure corresponding to the measured degree of compression. For example, the fluid accommodation portion 157 may be realized as a gas spring or a hydraulic cylinder.

A relationship between the measured degree of compression and the pressure may correspond to any one of the graphs of FIG. 10 as described above. However, exemplary embodiments are not limited thereto and a different relationship may be established according to embodiments.

In a case where compression of the breast is not completed ('NO' to operation 315), measuring and providing feedback of the degree of compression are repeated. When compression of the breast is completed ('YES' to operation 315), the compressing operation is terminated, and X-rays are emitted and detected to capture an X-ray image of the breast. In an exemplary embodiment, whether compression of the breast is completed may be determined by using a compression completion button or an X-ray imaging start button provided to the X-ray imaging apparatus 100.

In an X-ray imaging apparatus and a control method for the same according to the above exemplary embodiments, a user may indirectly feel the degree of compression of the breast, i.e., a patient, by transferring pressure corresponding to the degree of compression of the breast to the user, and more accurate compression considering the patient may be performed.

As described in the above, by transferring pressure corresponding to the degree of compression of the breast, the user may control force or pressure to be applied to the paddle manipulator 150 based on the degree of compression. Thereby, more safe compression considering the patient may be performed.

Exemplary embodiments may also be implemented through computer-readable recording media having recorded thereon computer-executable instructions such as program modules that are executed by a computer. Computer-readable media may be any available media that can be accessed by a computer and include both volatile and nonvolatile media and both detachable and non-detachable media. Examples of the computer-readable media may include a read-only memory (ROM), a random-access memory (RAM), a compact disc (CD)-ROM, a magnetic tape, a floppy disk, an optical data storage device, etc. Furthermore, the computer-readable media may include computer storage media and communication media. The computer storage media include both volatile and nonvolatile and both detachable and non-detachable media implemented by any method or technique for storing information such as computer-readable instructions, data structures, program modules or other data. The communication media typically embody computer-readable instructions, data structures, program modules, other data of a modulated data signal such as a carrier wave, or other transmission mechanism, and they include any information transmission media.

Although a few exemplary embodiments have been shown and described, it would be appreciated by those skilled in the art that changes may be made in these embodiments without departing from the principles and spirit of the disclosure, the scope of which is defined in the claims and their equivalents.

What is claimed is:

1. An X-ray imaging apparatus to capture an X-ray image of an object, the X-ray imaging apparatus comprising:
    an X-ray source configured to emit an X-ray onto the object;
    a detector assembly configured to detect the X-ray transmitted through the object;
    a compression paddle configured to compress the object positioned on the detector assembly;
    a paddle manipulator configured to control the compression paddle in response to an external force applied to the paddle manipulator in a first direction;
    a degree-of-compression sensor configured to measure a degree of compression to which the object is compressed by the compression paddle; and
    a pressure controller configured to supply a pressure corresponding to the measured degree of compression of the object to the paddle manipulator, the pressure being supplied to the paddle manipulator in a second direction opposite to the first direction.

2. The X-ray imaging apparatus according to claim 1, wherein the paddle manipulator comprises a fluid accommodation portion configured to accommodate a fluid therein,
    wherein the pressure controller controls an amount of the fluid accommodated in the fluid accommodation portion according to the degree of compression of the object.

3. The X-ray imaging apparatus according to claim 2, wherein the fluid accommodation portion comprises at least one from among a hydraulic cylinder and a gas spring.

4. The X-ray imaging apparatus according to claim 3, wherein the paddle manipulator further comprises an upper plate to which the external force is applied,
    wherein the fluid accommodation portion is positioned on a surface of the upper plate.

5. The X-ray imaging apparatus according to claim 4, wherein the paddle manipulator comprises a foot pedal.

6. The X-ray imaging apparatus according to claim 1, wherein the pressure supplied to the paddle manipulator is substantially linearly proportional to the degree of compression of the object.

7. The X-ray imaging apparatus according to claim 6, wherein a proportionality constant between the degree of compression of the object and the pressure supplied to the paddle manipulator is greater than 0 and equal to or less than 1.

8. The X-ray imaging apparatus according to claim 1, wherein the pressure controller supplies the pressure corresponding to the degree of compression of the object to the paddle manipulator such that a rate of increase of the pressure supplied to the paddle manipulator decreases in response to an increase in the degree of compression of the object.

9. The X-ray imaging apparatus according to claim 1, wherein the pressure controller supplies the pressure corresponding to the degree of compression of the object to the paddle manipulator such that a rate of increase of the pressure supplied to the paddle manipulator increases in response to an increase in the degree of compression of the object.

10. The X-ray imaging apparatus according to claim 2, wherein the degree-of-compression sensor comprises at least one from among a force sensor and a pressure sensor.

11. The X-ray imaging apparatus according to claim 10, wherein the degree-of-compression sensor is mounted on the compression paddle.

12. The X-ray imaging apparatus according to claim 10, wherein the degree-of-compression sensor measures the degree of compression of the object in real time or at a certain time interval.

13. The X-ray imaging apparatus according to claim 12, further comprising a display configured to numerically display the measured degree of compression of the object.

14. A control method of an X-ray imaging apparatus, the X-ray imaging apparatus comprising a compression paddle configured to compress an object, and a paddle manipulator configured to control the compression paddle in response to an external force applied to the paddle manipulator, the control method comprising:

moving, by the paddle manipulator, the compression paddle in response to the external force applied to the paddle manipulator in a first direction to compress the object;

measuring a degree of compression of the object; and supplying a pressure corresponding to the measured degree of compression of the object to the paddle manipulator, the pressure being supplied to the paddle manipulator in a second direction opposite to the first direction.

15. The control method according to claim 14, wherein the measuring is performed in real time or at a certain time interval.

16. The control method according to claim 14, wherein the supplying comprises supplying the pressure substantially linearly proportional to the degree of compression of the object.

17. The control method according to claim 14, wherein the supplying comprises supplying the pressure to the paddle manipulator such that a rate of increase of the pressure supplied to the paddle manipulator increases or decreases in response to an increase of the degree of compression.

18. An apparatus for controlling positioning a compression paddle to compress an object placed on a support base for use in an X-ray imaging apparatus, the apparatus comprising:

a paddle manipulator configured to control positioning the compression paddle in response to an external force applied to the paddle manipulator in a first direction;

a sensor configured to sense a pressure applied to the object by the compression paddle; and a controller configured to output a tactile feedback corresponding to the sensed pressure to the paddle manipulator, the tactile feedback being output to the paddle manipulator in a second direction opposite to the first direction.

19. The apparatus according to claim 18, wherein the paddle manipulator comprises a foot pedal, and wherein, when the foot pedal is pressed by a user, the controller outputs, as the tactile feedback, a reaction force from the foot pedal corresponding to the sensed pressure.

20. The apparatus according to claim 18, wherein the X-ray imaging apparatus comprises a breast imaging apparatus.

* * * * *